United States Patent
Key et al.

(10) Patent No.: US 11,754,545 B2
(45) Date of Patent: Sep. 12, 2023

(54) WATER QUALITY MONITOR SYSTEM AND METHOD

(71) Applicant: Pentair Water Pool and Spa, Inc., Cary, NC (US)

(72) Inventors: Adam Key, Cary, NC (US); Mitchell Bellamy, Cary, NC (US); Drake Fisher, Cary, NC (US)

(73) Assignee: PENTAIR WATER POOL & SPA, INC., Cary, NC (US)

( * ) Notice: Subject to any disclaimer, the term of this patent is extended or adjusted under 35 U.S.C. 154(b) by 635 days.

(21) Appl. No.: 16/801,434

(22) Filed: Feb. 26, 2020

(65) Prior Publication Data

US 2020/0271635 A1 Aug. 27, 2020

Related U.S. Application Data

(60) Provisional application No. 62/810,489, filed on Feb. 26, 2019.

(51) Int. Cl.
*G01N 33/18* (2006.01)
*H04L 67/12* (2022.01)
(Continued)

(52) U.S. Cl.
CPC ......... *G01N 33/1886* (2013.01); *G01K 3/005* (2013.01); *G01K 7/22* (2013.01);
(Continued)

(58) Field of Classification Search
CPC ........... G01N 33/1886; G01N 27/4167; G01N 27/4168; G01N 33/1893; G01K 3/005;
(Continued)

(56) References Cited

U.S. PATENT DOCUMENTS

D138,325 S * 7/1944 Pool ............................ D23/258
3,162,470 A * 12/1964 Owens ................... F16L 37/113
285/376
(Continued)

FOREIGN PATENT DOCUMENTS

CN 207215807 U 4/2018
CN 108226411 A 6/2018
(Continued)

OTHER PUBLICATIONS

Giffin, Wm. R., "Maintaining Swimming Pools, Spas, Whirlpool Tubs and Saunas", Cleaning Consultant Services, Inc., pp. 1-4, 2001.
(Continued)

*Primary Examiner* — Nathaniel T Woodward
*Assistant Examiner* — Philip L Cotey
(74) *Attorney, Agent, or Firm* — Husch Blackwell LLP (57) ABSTRACT

A water quality monitor system comprising a base having a first end and a second end is disclosed. A cover is removably coupled to the first end of the base such that the cover surrounds and covers the first end of the base. A flow cell jar is connected to the second end of the base. A sensor probe is connected to the second end of the base and extends downward into the flow cell jar. The sensor probe is configured to measure a plurality of water quality parameters. The base includes an inlet and an outlet connected to opposing ends of the base and connected in-line to the plumbing of a pool recirculation system. A controller is configured to provide a connection between the water quality monitor and a cloud-based storage system, using a wireless network. The measured water quality parameters are transmitted to the cloud storage system.

20 Claims, 3 Drawing Sheets (51) Int. Cl.
*G01K 3/00* (2006.01)
*G01K 7/22* (2006.01)
*G01K 13/02* (2021.01)
*G01N 27/416* (2006.01)
*C02F 103/42* (2006.01)
*E04H 4/14* (2006.01)

(52) U.S. Cl.
CPC ......... *G01K 13/02* (2013.01); *G01N 27/4167* (2013.01); *G01N 27/4168* (2013.01); *C02F 2103/42* (2013.01); *C02F 2209/008* (2013.01); *C02F 2209/02* (2013.01); *C02F 2209/04* (2013.01); *C02F 2209/06* (2013.01); *E04H 4/14* (2013.01); *G01K 13/026* (2021.01); *G01N 33/1893* (2013.01); *H04L 67/12* (2013.01)

(58) Field of Classification Search
CPC ........ G01K 7/22; G01K 13/02; G01K 13/026; C02F 2103/42; C02F 2209/008; C02F 2209/02; C02F 2209/04; C02F 2209/06; E04H 4/14; H04L 67/12
See application file for complete search history.

(56) References Cited

U.S. PATENT DOCUMENTS

| | | | | | |
|---|---|---|---|---|---|
| D242,618 | S * | 12/1976 | Milo | ............................ | D23/247 |
| 4,033,871 | A * | 7/1977 | Wall | ....................... | G05D 21/02 |
| | | | | | 210/756 |
| D254,266 | S * | 2/1980 | Tableriou | ..................... | D23/262 |
| 4,224,154 | A * | 9/1980 | Steininger | ............... | C02F 1/008 |
| | | | | | 210/85 |
| 4,435,095 | A * | 3/1984 | Jones | ..................... | G01K 13/00 |
| | | | | | 362/802 |
| 4,510,487 | A * | 4/1985 | Wolfe | .................. | G08B 21/084 |
| | | | | | 367/178 |
| 4,752,740 | A * | 6/1988 | Steininger | .......... | G01N 27/4168 |
| | | | | | 324/438 |
| 4,781,810 | A * | 11/1988 | Tucker | ...................... | C02F 5/02 |
| | | | | | 204/266 |
| 4,801,886 | A * | 1/1989 | Steininger | .......... | G01N 27/4168 |
| | | | | | 324/438 |
| 4,825,207 | A * | 4/1989 | Snell | ....................... | G08B 19/00 |
| | | | | | 340/3.7 |
| 4,900,432 | A * | 2/1990 | Arnold | .................. | E04H 4/1263 |
| | | | | | 210/91 |
| 4,940,946 | A * | 7/1990 | Nazaryan | ............. | G01N 33/182 |
| | | | | | 324/438 |
| 5,055,183 | A * | 10/1991 | Buchan | ................... | C02F 1/688 |
| | | | | | 210/85 |
| 5,115,222 | A * | 5/1992 | Peralta | ................. | G08B 21/082 |
| | | | | | 340/625 |
| 5,124,960 | A * | 6/1992 | Miller | ..................... | G04G 21/00 |
| | | | | | 368/278 |
| 5,152,610 | A * | 10/1992 | Hallett | ....................... | E04H 4/14 |
| | | | | | 374/208 |
| 5,169,236 | A * | 12/1992 | Iest | ........................ | G01K 1/08 |
| | | | | | 374/E1.008 |
| 5,189,350 | A * | 2/1993 | Mallett | .................... | G01D 1/14 |
| | | | | | 318/434 |
| 5,326,481 | A * | 7/1994 | Alwerud | .................. | C02F 1/686 |
| | | | | | 702/100 |
| 5,422,014 | A * | 6/1995 | Allen | ...................... | C02F 1/008 |
| | | | | | 210/743 |
| 5,518,635 | A * | 5/1996 | Kohlman | ............... | E04H 4/1281 |
| | | | | | 210/749 |
| D371,824 | S * | 7/1996 | Price | ............................ | D23/207 |
| 5,616,239 | A * | 4/1997 | Wendell | .................. | B01D 37/02 |
| | | | | | 210/167.13 |
| 5,681,110 | A * | 10/1997 | Burzacchi | ................ | G01K 1/06 |
| | | | | | 374/208 |
| 5,788,826 | A * | 8/1998 | Nyberg | ................. | C02F 1/4693 |
| | | | | | 204/632 |
| 5,798,940 | A * | 8/1998 | Bratton | .................. | G01V 9/007 |
| | | | | | 702/30 |
| 5,895,565 | A * | 4/1999 | Steininger | ............... | C02F 1/008 |
| | | | | | 210/85 |
| 5,898,940 | A * | 5/1999 | Cameron | ............... | A41B 13/10 |
| | | | | | 2/48 |
| 5,996,138 | A * | 12/1999 | Kentch | .................. | E04H 4/1209 |
| | | | | | 4/488 |
| 6,003,164 | A * | 12/1999 | Leaders | .................. | C02F 1/008 |
| | | | | | 4/496 |
| 6,113,858 | A * | 9/2000 | Tang | ...................... | G01N 21/78 |
| | | | | | 436/163 |
| D432,206 | S * | 10/2000 | Stoltz | .......................... | D23/209 |
| 6,125,481 | A * | 10/2000 | Sicilano | ............... | E04H 4/1209 |
| | | | | | 210/94 |
| D439,313 | S * | 3/2001 | Wey | ............................ | D23/236 |
| 6,223,359 | B1 * | 5/2001 | Oltmanns | .................. | E04H 4/12 |
| | | | | | 137/392 |
| 6,225,900 | B1 * | 5/2001 | Keon | ....................... | G08B 1/08 |
| | | | | | 340/384.1 |
| 6,228,272 | B1 * | 5/2001 | Gola | ......................... | E04H 4/12 |
| | | | | | 210/138 |
| 6,238,553 | B1 * | 5/2001 | Lin | .......................... | B01F 21/22 |
| | | | | | 210/85 |
| 6,253,227 | B1 * | 6/2001 | Tompkins | .......... | G05D 23/1931 |
| | | | | | 709/201 |
| 6,294,086 | B1 * | 9/2001 | Reeves | .................. | B01F 21/22 |
| | | | | | 210/91 |
| 6,309,538 | B1 * | 10/2001 | Khan | ................... | G01N 33/1886 |
| | | | | | 210/85 |
| 6,340,431 | B2 * | 1/2002 | Khan | ................... | G01N 33/1886 |
| | | | | | 210/85 |
| 6,476,721 | B1 * | 11/2002 | Diebold | ................. | G08B 21/088 |
| | | | | | 340/573.6 |
| 6,579,446 | B1 * | 6/2003 | Teran | ........................ | C02F 1/50 |
| | | | | | 210/85 |
| 6,625,824 | B1 * | 9/2003 | Lutz | .......................... | E04H 4/12 |
| | | | | | 137/625.21 |
| 6,653,842 | B2 * | 11/2003 | Mosley | ............... | G01N 27/4168 |
| | | | | | 324/438 |
| 6,697,706 | B2 * | 2/2004 | Gardner, Jr. | ........ | A47L 15/0055 |
| | | | | | 700/244 |
| 6,713,298 | B2 * | 3/2004 | McDevitt | ........... | G01N 21/6428 |
| | | | | | 435/287.8 |
| D489,431 | S * | 5/2004 | Antunez | ..................... | D23/236 |
| 6,792,956 | B2 * | 9/2004 | Bredo | .................... | E04H 4/1654 |
| | | | | | 134/44 |
| 6,900,736 | B2 * | 5/2005 | Crumb | ................... | G08C 19/24 |
| | | | | | 4/492 |
| 6,958,693 | B2 * | 10/2005 | Rothgeb | .................. | C02F 1/008 |
| | | | | | 340/539.22 |
| 7,037,038 | B1 * | 5/2006 | Haski | .................... | E04H 4/1263 |
| | | | | | 405/60 |
| D526,382 | S * | 8/2006 | Thompson | .................. | D23/208 |
| 7,094,353 | B2 * | 8/2006 | Unhoch | .................. | G01F 13/006 |
| | | | | | 210/759 |
| 7,167,087 | B2 * | 1/2007 | Corrington | .......... | G08B 26/007 |
| | | | | | 340/505 |
| D537,913 | S * | 3/2007 | Biberger | ..................... | D23/208 |
| 7,292,898 | B2 * | 11/2007 | Clark | ................... | G01N 33/1886 |
| | | | | | 700/20 |
| D559,943 | S * | 1/2008 | Mercer | ........................ | D23/207 |
| 7,391,333 | B2 * | 6/2008 | Madden | .................. | G01N 33/18 |
| | | | | | 73/61.41 |
| 7,398,138 | B2 * | 7/2008 | Emery | .................... | C02F 1/008 |
| | | | | | 700/282 |
| 7,681,436 | B2 * | 3/2010 | Biberger | ................. | G01N 33/18 |
| | | | | | 73/61.41 |
| 7,752,893 | B2 * | 7/2010 | Biberger | ................. | G01N 33/18 |
| | | | | | 73/61.41 |
| 7,938,909 | B2 * | 5/2011 | Mortimer | ............... | C02F 1/008 |
| | | | | | 134/169 C |
| 7,993,600 | B2 * | 8/2011 | Doyle | ...................... | C01D 3/04 |
| | | | | | 422/256 |

(56) References Cited

U.S. PATENT DOCUMENTS

| | | | | |
|---|---|---|---|---|
| 8,281,647 B2* | 10/2012 | Boutet | | E04H 4/12 |
| | | | | 73/61.41 |
| 8,323,486 B2* | 12/2012 | Andrews | | C02F 1/74 |
| | | | | 210/232 |
| 8,347,427 B2* | 1/2013 | Klicpera | | B05B 12/12 |
| | | | | 4/643 |
| 8,459,100 B2* | 6/2013 | Biberger | | G01N 33/18 |
| | | | | 73/61.41 |
| 9,097,234 B2* | 8/2015 | Breau | | F03B 13/10 |
| 9,494,480 B2* | 11/2016 | Klicpera | | G01M 3/00 |
| 9,635,442 B1* | 4/2017 | Chen | | G01N 33/18 |
| 9,776,888 B1* | 10/2017 | Kurani | | C02F 1/66 |
| 9,784,686 B2* | 10/2017 | Clark | | G01N 21/6428 |
| 9,834,451 B2* | 12/2017 | Miller | | C02F 1/766 |
| 9,858,792 B2* | 1/2018 | Fernandes | | E04H 4/00 |
| 9,926,207 B2* | 3/2018 | Rodriguez | | C02F 1/008 |
| 10,150,680 B1* | 12/2018 | Kurani | | G01N 33/18 |
| 10,287,180 B1* | 5/2019 | Kurani | | C02F 1/66 |
| 10,329,784 B1* | 6/2019 | Corwin | | E04H 4/1236 |
| 2001/0045380 A1* | 11/2001 | Khan | | C02F 1/008 |
| | | | | 210/85 |
| 2002/0035403 A1* | 3/2002 | Clark | | G05B 23/027 |
| | | | | 700/19 |
| 2002/0195403 A1* | 12/2002 | Takeda | | B01J 49/85 |
| | | | | 210/96.1 |
| 2003/0205509 A1* | 11/2003 | Barnes | | C02F 1/325 |
| | | | | 210/85 |
| 2003/0227394 A1* | 12/2003 | Rothgeb | | A47L 15/4297 |
| | | | | 340/870.01 |
| 2004/0031329 A1* | 2/2004 | Carpenter | | G01F 23/26 |
| | | | | 73/861.19 |
| 2004/0066313 A1* | 4/2004 | Ong | | G08C 19/04 |
| | | | | 340/870.11 |
| 2004/0197229 A1* | 10/2004 | Runyon | | G01N 33/18 |
| | | | | 422/63 |
| 2004/0208499 A1* | 10/2004 | Grober | | F16M 11/18 |
| | | | | 396/428 |
| 2005/0167345 A1* | 8/2005 | De Wet | | C02F 1/008 |
| | | | | 210/791 |
| 2005/0220169 A1* | 10/2005 | McGowan-Scanlon | | G01K 1/14 |
| | | | | 374/E1.018 |
| 2005/0225766 A1* | 10/2005 | Hansen | | G01N 15/1463 |
| | | | | 356/436 |
| 2005/0279677 A1* | 12/2005 | Lin | | C02F 1/688 |
| | | | | 210/85 |
| 2005/0288821 A1* | 12/2005 | Laflamme | | A61H 33/005 |
| | | | | 700/275 |
| 2006/0096927 A1* | 5/2006 | Clukies | | B01D 17/02 |
| | | | | 210/171 |
| 2006/0241874 A1* | 10/2006 | Carter | | G05D 9/12 |
| | | | | 702/50 |
| 2006/0292043 A1* | 12/2006 | Biberger | | G01N 33/18 |
| | | | | 73/53.01 |
| 2007/0219652 A1* | 9/2007 | McMillan | | A01K 63/04 |
| | | | | 700/83 |
| 2010/0096338 A1* | 4/2010 | De Wet | | E04H 4/12 |
| | | | | 210/103 |
| 2010/0250449 A1 | 9/2010 | Doyle et al. | | |
| 2010/0332149 A1* | 12/2010 | Scholpp | | C02F 1/008 |
| | | | | 702/188 |
| 2013/0126403 A1* | 5/2013 | Kilawee | | C02F 1/687 |
| | | | | 210/96.1 |
| 2016/0012705 A1 | 1/2016 | Baret | | |
| 2017/0215261 A1* | 7/2017 | Potucek | | H05B 47/105 |
| 2017/0235318 A1* | 8/2017 | Bright | | G05D 7/0635 |
| | | | | 137/2 |
| 2017/0248568 A1* | 8/2017 | Yizhack | | G01N 21/3577 |
| 2018/0240322 A1* | 8/2018 | Potucek | | E04H 4/14 |
| 2018/0284758 A1* | 10/2018 | Cella | | G06N 3/084 |
| 2019/0025273 A1* | 1/2019 | Brondum | | G01N 27/07 |
| 2019/0135657 A1* | 5/2019 | Yates | | E03B 7/078 |
| 2019/0353156 A1* | 11/2019 | Ward | | F04D 13/08 |
| 2021/0298557 A1* | 9/2021 | Budampati | | G01M 3/26 |

FOREIGN PATENT DOCUMENTS

| | | |
|---|---|---|
| DE | 19810400 A1 | 9/1999 |
| DE | 19921436 A1 | 11/2000 |
| EP | 821514 A1 | 1/1998 |
| EP | 1847513 A1 | 10/2007 |
| FR | 2932207 A1 | 12/2009 |
| KR | 20130048613 A | 12/2004 |
| KR | 101261553 B1 | 4/2013 |
| KR | 20040102712 A | 5/2015 |
| WO | 03087501 A1 | 10/2003 |
| WO | 03091668 A2 | 11/2003 |
| WO | 2010051842 A1 | 5/2010 |
| WO | 2018198018 A1 | 11/2018 |

OTHER PUBLICATIONS

"Water Chemistry for Swimming Pools," North Carolina Department of Environment and Natural Resources, available on the Internet archive at <http://web-archive.org/>, Dec. 19, 2002, 12 pgs.

Examination Report issued for European Patent Application No. 20159540.2 dated Sep. 30, 2022, 7 pages.

* cited by examiner

WATER QUALITY MONITOR SYSTEM AND METHOD

RELATED APPLICATIONS

This application claims priority under 35 U.S.C. § 119 to U.S. Provisional Application No. 62/810,489 filed on Feb. 26, 2019, the entire disclosure of which is incorporated herein by reference.

BACKGROUND

Homeowners may struggle to control the quality of the water in aquatic applications such as swimming pools. (As used throughout, aquatic applications include at least swimming pools, spas, hot tubs, and the like.) The water chemistry may be affected by one or more of environmental factors and weather conditions (e.g., rain, sunlight, hail, wind, pollen, debris, and the like) and human elements (e.g., bacteria, urine, and sweat). In order to account for these factors, a user may adjust the chemical properties of their pool on a weekly (or more frequent basis), which may result in providing too much disinfectant or other chemical agents. Ultimately, water that is out of chemical balance may irritate skin, hair, or clothing. Often, additional chemicals may need to be added to maintain the pH at an acceptable level.

In some known systems, a water quality monitor may be provided in a housing designed to float on the surface of the water of the pool. These systems suffer from numerous drawbacks, however. For example, a floating system may interfere with swimmers or others in the water. Further, the user may need to enter the swimming pool to access the floating system to read the measurements.

SUMMARY

Accordingly, there exists a need for a system and method to provide pool owners and pool servicers with an enhanced system and method for in-line monitoring of water quality parameters.

Some embodiments provide for a water quality monitor system comprising a base having a first end and a second end. A cover is removably coupled to the first end of the base such that the cover surrounds and covers the first end of the base. A flow cell jar is connected to the second end of the base and a sensor probe is connected to the second end of the base and extends downwardly into the flow cell jar. The sensor probe is configured to measure a plurality of water quality parameters. The base further includes an inlet and an outlet connected to opposing ends of the base and connected in-line to the plumbing of a swimming pool recirculation system. A controller is configured to provide a connection between the water quality monitor and a cloud-based storage system, using a wireless network. The measured water quality parameters may be transmitted through the wireless network to the cloud storage system.

In some forms, the plurality of water quality parameters comprises pH, oxidation reduction potential, and temperature. The water quality monitor can be mounted to an equipment pad. The water quality monitor can include a removable antenna. The water quality monitor can include a removable and rechargeable battery pack. The water quality monitor can include an inlet flow control valve in fluid communication with the inlet and an outlet flow control valve in fluid communication with the outlet. The water quality monitor can include a first tube connector and a second tube connector. In some forms, the first tube connector is configured to connect the inlet and the inlet flow control valve to a first side of the base, and the second tube connector is configured to connect the outlet and the outlet flow control valve to a second side of the base. The water quality monitor can include a flow switch, and the water quality monitor can be configured to periodically check the flow switch for water flow through the swimming pool recirculation system. The water quality monitor can include a wake/pair button configured to return the water quality monitor to fully active operation from reduced power consumption upon actuation of the wake/pair button. The wake/pair button can be configured to pair the water quality monitor with an external electronic device upon actuation of the wake/pair button.

Other embodiments provide for a method for remotely monitoring water quality parameters in a pool using a water quality monitor. The method includes the steps of connecting the water quality monitor in-line with a recirculation system of the swimming pool, determining whether there is sufficient flow through the water quality monitor, measuring water quality parameters using a sensor probe, connecting to a wireless internet connection, transmitting the measured water quality parameters through the wireless internet connection to a cloud storage system, and displaying the measured water quality parameters on a web-based application.

In some forms, the method can include notifying a user of one of improper swimming pool function or proper swimming function. The method can include receiving information about a size of the swimming pool. The method can include periodically rechecking whether there is sufficient fluid flow through the water quality monitor. The method can include periodically rechecking whether there is sufficient fluid flow through the water quality monitor is performed at least once every 15 minutes. The plurality of water quality parameters can include pH, oxidation-reduction potential, and temperature. The method can include receiving a predetermined set of values defined for one or more of pH, oxidation-reduction potential, and temperature. The method can include comparing, at the cloud-based storage system, one or more of measured pH, oxidation-reduction potential, or temperature to the predetermined set of values defined for one or more of pH, oxidation-reduction potential, and temperature. The method can include displaying the comparison of the plurality of water quality parameters to the set of predetermined values. The method can include periodically reconnecting to the wireless internet connection to transmit the plurality of water quality parameter through the wireless internet connection to the cloud storage system.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise specified or limited, "at least one of A, B, and C," and similar other phrases, are meant to indicate A, or B, or C, or any combination of A, B, and/or C. As such, this phrase, and similar other phrases can include single or multiple instances of A, B, and/or C, and, in the case that any of A, B, and/or C indicates a category of elements, single or multiple instances of any of the elements of the categories A, B, and/or C.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Figure 1:
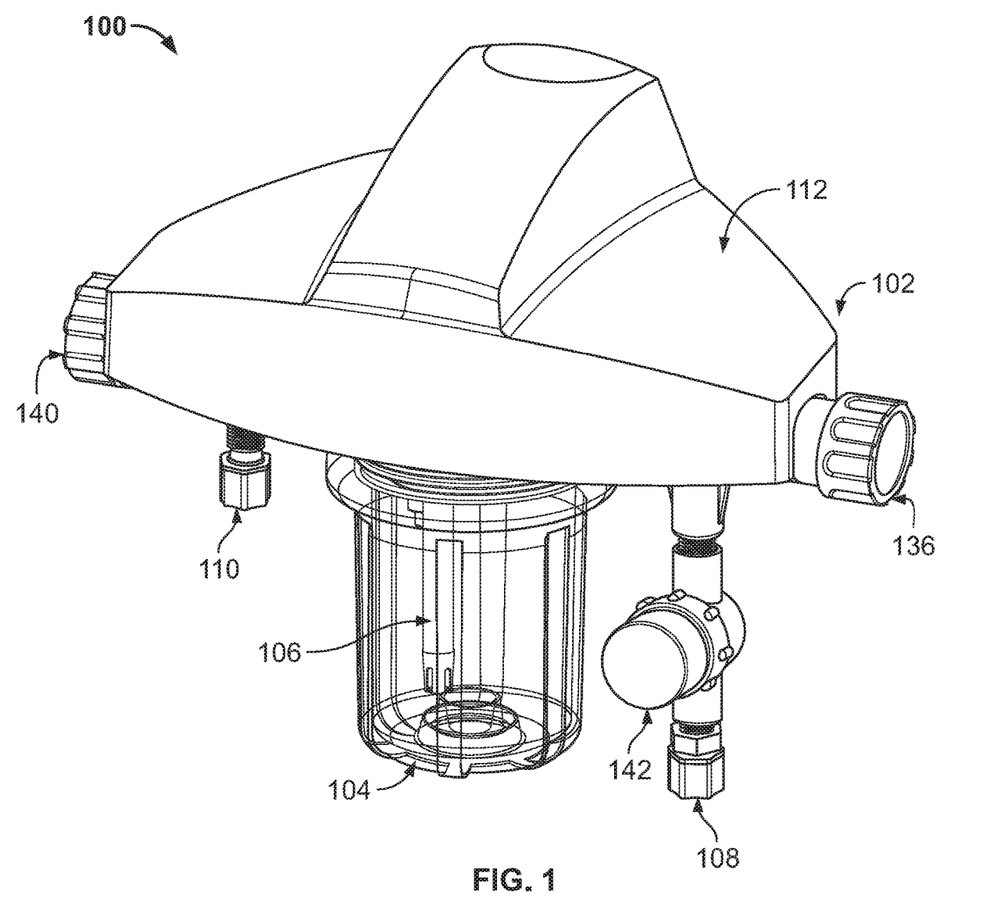
FIG. 1 is an isometric view of a water quality monitor system according to one embodiment of the invention.
Figure 2:
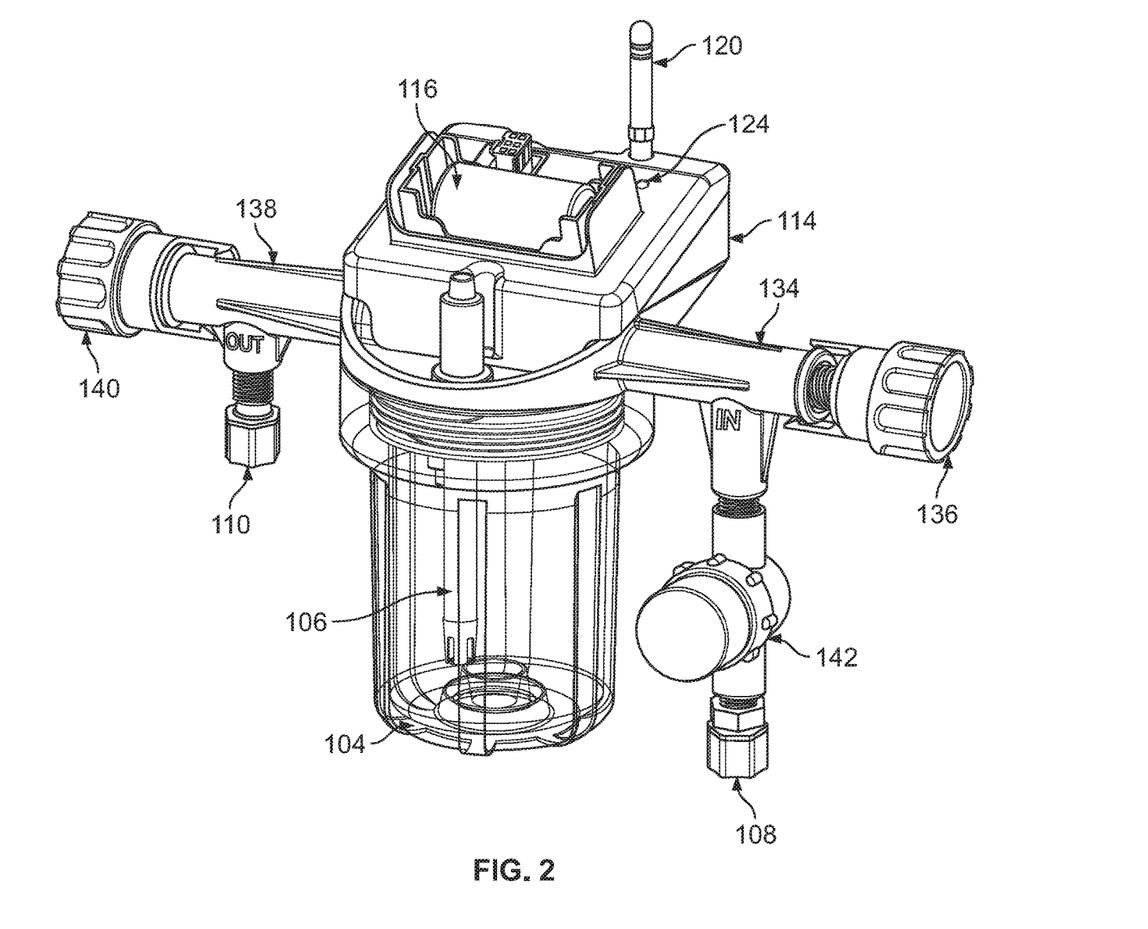
FIG. 2 is an isometric view of the water quality monitor system of FIG. 1, with the cover removed for clarity.
Figure 3:
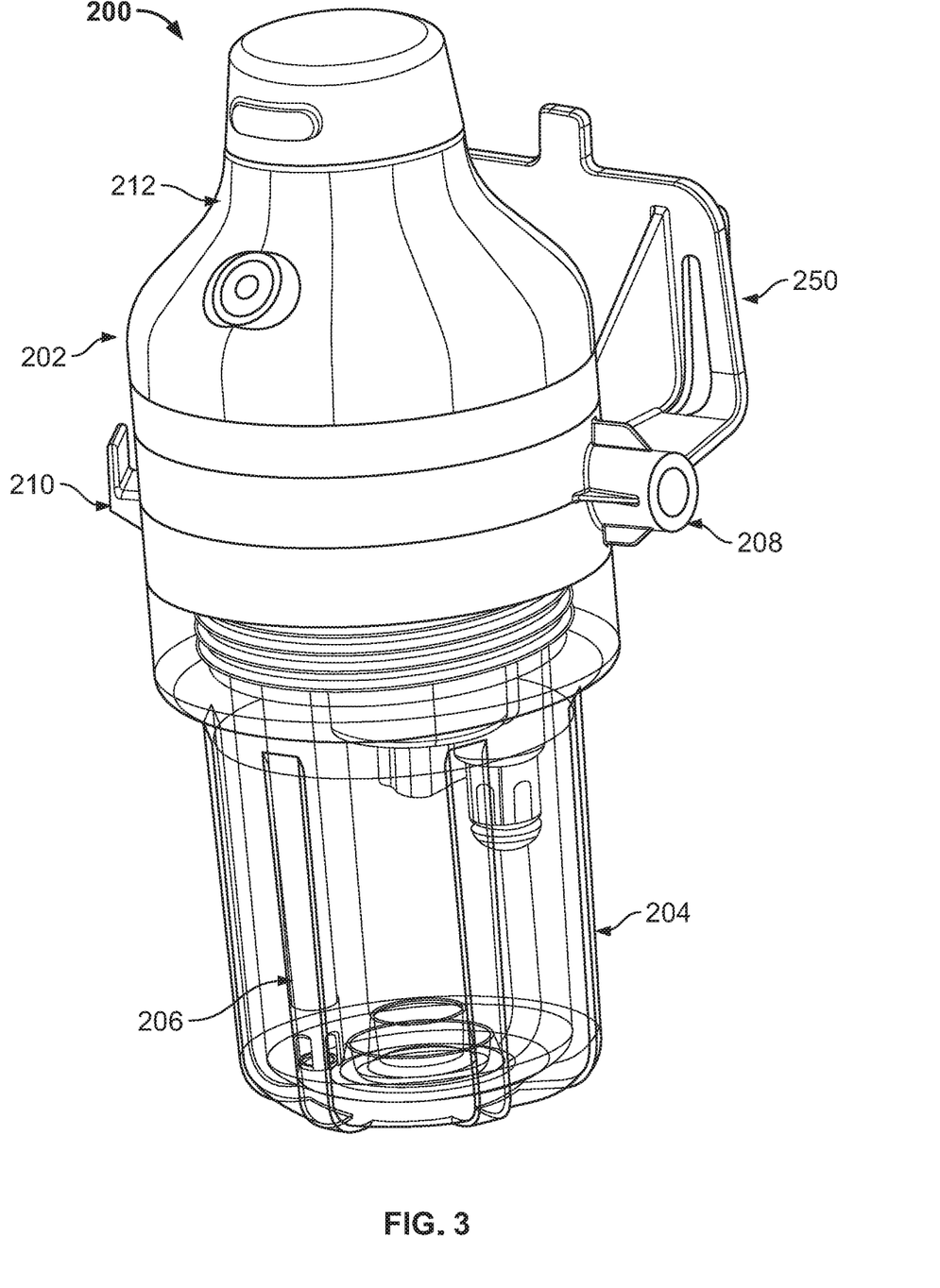
FIG. 3 is an isometric view of a water quality monitor system according to another embodiment.

FIGS. 1-3 illustrate a water quality monitor system 100, according to some embodiments. The water quality monitor 100 is configured and designed to monitor water quality parameters of a residential or commercial aquatic fluid system (such as a swimming pool, spa, hot tub, and other applications where a body of water is confined by a barrier). The water quality monitor 100 is designed to report a water quality status and/or one or more water quality parameters based on measurements of the water quality parameters, to a user. In some embodiments, the measured water quality parameters may include one or more of pH, oxidation-reduction potential (ORP), temperature, and/or other water parameters, and combinations thereof. In one embodiment, the water quality monitor 100 measures pH, ORP, and temperature and may utilize a single probe to do so. The measurements may be taken at a predefined time period (e.g., about every 5 minutes, about every 10 minutes, about every 15 minutes) and transmitted to a user.

FIG. 1 illustrates the water quality monitor system 100 that may be provided in the form of a base 102, a flow cell jar 104, a sensor probe assembly 106, a water inlet 108, and a water outlet 110. The base 102 may include a removable cover 112 configured to protect the internal components of the water quality monitor 100 from environmental conditions. The base 102 and cover 112 may comprise any shape, configuration and/or cross section (e.g., the base 102 and cover 112 may be oblong shaped as depicted in FIGS. 1 and 2 or conically tapered as depicted in FIG. 3).

The cover 112 may be removably coupled to the base 102. For example, the cover 112 may be completely detachable from the base 102 of the water quality monitor. In other embodiments, the cover 112 may be hingedly attached at one end to the base 102 such that the cover 112 may be rotated about a hinge or other pivot point. In this case, the cover 112 may be attached to the base 102 at a rear end, allowing the user to move the cover 112 from a closed position to an open position without fully detaching the cover 112. In other embodiments, the cover 112 may be attached to the base 102 via threads or through an interference fit. During normal operation of the water quality monitor, the cover 112 is in the closed position. The cover 112 may be manufactured using any material suitable for providing adequate protection from natural elements such as wind and rain. The cover 112 may be attached to the base 102 of the water quality monitor using any suitable means.

FIG. 2 depicts a configuration showing when the cover 112 is moved to the open position, or is completely detached from the water quality monitor. In this configuration, the internal components of the base 102 are exposed. The base 102 may include an intermediate cover 114 having a top side and a bottom side. In some embodiments, one or more portions of the base 102 and/or cover 112 may include a power assembly for providing power to the water quality monitor 100. For example, in some embodiments, the top side of the intermediate cover 114 contains a battery 116 for providing power to the water quality monitor 100. In some embodiments, the battery 116 is a lithium battery. The battery 116 may be single use or may be rechargeable. In some embodiments, the rechargeable battery 116 may have a battery life of at least one year. In other embodiments, the rechargeable battery 116 has a battery life of at least 2 years. The system may measure the battery life periodically during operation (e.g., the period may be set to measure battery life about once per hour, once per day, once per week, or some other pre-defined time period). The battery 116 also may be removed from the base 102 for replacement or for recharging and may be purchased where any commonly available batteries are sold. In other embodiments, the battery 116 may be custom made and not commonly available.

In other embodiments, the power supply to the water quality monitor system 100 may be hard wired and/or designed to integrate with another pool component. For example, the power supply may be hard wired to an external controller and/or other automation equipment. In one embodiment, the power supply for the water quality monitor system 100 may be integrated into the power supply of the external controller (e.g., EasyConnect or IntelliConnect). The power supply may also be configured to connect directly to a conventional power outlet, providing, for example, a nominal voltage of 120V.

The water quality monitor 100 also includes an antenna 120 and an antenna cable (not pictured) attached to the top side of and protruding from the intermediate cover 114. In some embodiments, the antenna 120 may be removable and mounted on other portions of the base 102. In other embodiments, the antenna 120 is externally mounted away from the water quality monitor 100. The removable antenna 120 may be protected under the cover 112, but can be removed and an extension cable (not pictured) can be installed to allow relocation of the antenna 120 away from the water quality monitor 100.

Still referring to FIG. 2, the water quality monitor 100 may also include a wake/pair button 124 arranged on the intermediate cover 114 configured to return the water quality monitor 100 to fully active operation from a "sleep mode", which comprises reduced functionality or power consumption, or to pair the water quality monitor 100 with an external electronic device when the button is pressed by the user. The wake/pair button 124 may also include an LED component and an internal factory reset button. In some embodiments, the water quality monitor 100 may also include a flow indicator (not shown) and a flow indicator cover.

The water quality monitor 100 may also include a controller (not shown) in communication with the base 102 and configured to connect the water quality monitor 100 to a cloud based storage system using a wireless network. The controller may comprise a printed circuit board assembly (not shown) configured to connect one or more electronic components of the water quality monitor 100. The printed circuit board assembly may include a Wi-Fi/Bluetooth chipset. In some embodiments, the chipset may be ESP32 and may be compatible with Amazon web services.

The controller may also include a flow switch configured to communicate an operational status to the device when adequate flow is occurring. In some embodiments, the flow switch may be a magnetic reed switch. The water quality monitor 100 may "wake up" periodically to check for water flow through the system. If there is flow, the water quality monitor 100 will record measurements of one or more water quality parameters. If there is no flow, or too little flow, the water quality monitor 100 will return to "sleep" until the beginning of another period. The flow measurements may be taken at a predefined time period (e.g., about every 5 minutes, about every 10 minutes, about every 15 minutes). The controller may also be configured to determine whether the system is electrically coupled to a conventional power outlet and power the water quality monitor 100 with one of the battery 116 or the conventional power outlet accordingly.

FIG. 2 depicts the sensor probe 106 protruding away from the bottom end of the base 102 and extending into and being surrounded by the flow cell jar 104. The sensor probe 106 is configured to measure the water quality parameters of water flowing through the water quality monitor 100. In some embodiments, the sensor probe 106 may be provided as a single probe that is designed to measure one or more of the pH value of the water, the oxidation-reduction potential of the water, water temperature, and combinations thereof. In one embodiment, the sensor probe 106 is a single 3-in-1 probe configured to measure the pH, ORP, and water temperature of the water flowing through the system.

In some forms, the sensor probe 106 includes a pH electrode having two half cells to detect pH, a glass pH ball at the end of the probe, and a reference electrode within the body of the probe. The pH electrode measures the unknown hydrogen ion content of the water with the use of a known hydrogen ion content reference solution.

The sensor probe 106 also includes an ORP sensor that is designed to measure the oxidative activity of dissolved agents. In some embodiments, the dissolved agents may be dissolved oxygen. The ORP sensor may be made of silver, which loses electrons to the oxidizer. The voltage ORP level may be directly correlated to how much oxidizer is in the solution. The sensor probe 106 may also include a silver salt gel solution within the probe. The silver salt gel solution is used as a reference of known ORP. The ORP of the water flowing through the water quality monitor 100 may be calculated by determining the oxidation level of the water with the use of the known ORP of the silver salt gel solution oxidation level. In some embodiments, the silver salt is silver chloride.

The sensor probe 106 may also include a temperature sensor for measuring the water temperature. In some embodiments, the temperature sensor may be a resistor that changes resistance depending on its environmental temperature. In some embodiments, the temperature sensor may be a NTC-10 k type thermistor.

The sensor probe 106 extends from the bottom end of the base 102 into the flow cell jar 104. The flow cell jar 104 is designed to hold water that is undergoing testing by the sensor probe 106. In some instances, the flow cell jar 104 is transparent or translucent to allow viewing of the sensor probe 106 and water that is being tested, without removing the flow cell jar 104 from the base 112. The flow cell jar 104 may be provided in the form of a cylindrical cup that is designed to be releasably attached to the base 102. For example, the base 102 and the flow cell jar 104 may comprise separate elements that are coupled together using conventional coupling techniques (e.g., threads, interference fit, tongue and grove, or other joining mechanisms). In other embodiments, the base 102 and the flow cell jar 104 may be manufactured as a single unit. The flow cell jar 104 may comprise any shape, configuration and/or cross section. The flow cell jar 104 may also include a drain plug (not shown) configured to allow water to be removed from the flow cell jar 104.

The base 102 of the water quality monitor 100 is in communication with an external water source through a water inlet 108 and a water outlet 110. The inlet 108 and outlet 110 are configured to allow water to pass through the water quality monitor system 100. The inlet 108 is in fluid communication with a first tube connector 134 and an inlet flow control valve 136. The outlet 110 is in fluid communication with a second tube connector 138 and an outlet flow control valve 140. In some embodiments, the first and second tube connectors 134, 138 have a t-shaped configuration. The first tube connector 134 is configured to connect the inlet 108 and the inlet flow control valve 136 to a first side of the base 102 and the second tube connector 138 is configured to connect the outlet 108 and the outlet flow control valve 140 to a second side of the base 102.

A debris filter 142 may be provided within the fluid flow path between the inlet 108 and the first side of the base 102. The debris filter 142 is designed to collect debris in the water, allowing for unimpeded flow of water through the water quality monitor 100. As illustrated in FIGS. 1 and 2, the water inlet 108 and the water outlet 110 may protrude downwardly from the bottom end of the base 102.

The water quality monitor 100 is designed to be connected in-line to the plumbing of a pool or aquatic system (e.g., a pool pump, a pool filter, and the like) and is in fluid communication with an external water source. Once the water quality monitor 100 is incorporated into the fluid flow path (e.g., pool return line) of the swimming pool recirculation system, water flows into the water quality monitor 100 at the inlet 108 and passes through the flow cell jar 104. The water then moves from the flow cell jar 104 and out of the system through the outlet 110.

In some embodiments, the water quality monitor 100 may be mounted to a vertical surface. For example, the water quality monitor 100 may be mounted to an equipment pad out of the reach of children and may not be readily visible to the user. In some embodiments, the tubing may be attached or otherwise secured by being strapped on to the pipe. In other embodiments, the water quality monitor 100 may be attached using any attachment method.

FIG. 3 illustrates a water quality monitor system 200 that is substantially similar to the embodiment depicted in FIG. 1, except for the differences discussed below. The water quality monitor 200 may generally include a base 202, a flow cell jar 204, and a sensor probe 206. The base 202 may include a tapered conical cover 212. A top portion of the base 202 and the cover 212 may be substantially the same shape such that the cover 212 fits over and encloses the top portion of the base 202. The water quality monitor 200 may further include a water inlet 208 and a water outlet 210 that do not include tube connectors. Instead, the inlet 208 and outlet 210 may be directly connected to the base 202. As further illustrated in FIG. 3, the water quality monitor 200 may include a mount 250 disposed on the back side of the base that is configured to provide support for the water quality monitor while it is mounted.

In use, the water quality monitor 100, 200 may be configured to wake itself from sleep mode every 15 minutes to check for flow through the use of a magnetic reed switch. If there is no flow, or the flow is too low, the water quality monitor 100, 200 will return to sleep mode. Once adequate flow has been established, the water quality monitor 100, 200 will measure one or more water quality parameters of the water system. In some embodiments, the water quality parameters are water temperature, pH, and ORP. The data associated with the water quality parameters may be collected and sent to a cloud environment to be accessed by a web-based browser interface. The web-based browser interface may include one or more of Android, IOS, and other web based browser interfaces.

The water quality monitor 100, 200 may periodically establish an internet connection in order to collect data and report data. In some embodiments, the water quality monitor 100, 200 may connect to the internet every 2 hours and report the last two hours' worth of collected data. In other embodiments, the water quality monitor 100, 200 may report the collected data every hour. The data may be transmitted by using a Wi-Fi connection via a router and the user may access the data using a web based application (App). The App may be designed to notify the user that the aquatic system (e.g., pool) is functioning properly or if it needs attention. The user may see the water temperature, pH, and ORP level associated with color indication of status of each component. In some embodiments, the App will notify the user that their water system is functioning properly or if the water system is in need of attention. During initial set-up of the App, the user may input additional information such as the size of the residential or commercial aquatic fluid system and/or chlorine levels. Inputting the additional information may allow the App to provide the user with recommended actions to take, based on the measured water quality parameters.

In some embodiments, a predetermined set of values is defined for one or more of the water temperature, pH, and ORP level into the cloud based storage system. The data collected by the water quality monitor 100, 200 can be transmitted to the cloud-based storage system, and a comparison of the data to the predetermined set of values can be performed at the cloud based storage system. The user may then access the result of this comparison via the App, where the comparison can be displayed to the user.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

The invention claimed is:

1. A method for remotely monitoring water quality parameters in a swimming pool using a water quality monitor, the method comprising:
   connecting an inlet and an outlet of the water quality monitor in-line with a recirculation system of the swimming pool;
   determining whether there is sufficient fluid flow through the water quality monitor;
   measuring a plurality of water quality parameters using a sensor probe;
   connecting to a wireless internet connection;
   transmitting the plurality of water quality parameters through the wireless internet connection to a cloud storage system; and
   displaying the plurality of water quality parameters on a web-based application.

2. The method of claim 1, further including the step of notifying a user of one of improper swimming pool function or proper swimming function.

3. The method of claim 1, further comprising receiving information about a size of the swimming pool.

4. The method of claim 1, further comprising periodically rechecking whether there is sufficient fluid flow through the water quality monitor.

5. The method of claim 4, wherein the step of periodically rechecking whether there is sufficient fluid flow through the water quality monitor is performed at least once every 15 minutes.

6. The method of claim 1, wherein the plurality of water quality parameters comprises pH, oxidation-reduction potential, and temperature.

7. The method of claim 6, further comprising receiving a predetermined set of values defined for one or more of pH, oxidation-reduction potential, and temperature.

8. The method of claim 7, further comprising comparing, at the cloud storage system, one or more of measured pH, oxidation-reduction potential, or temperature to the predetermined set of values defined for one or more of pH, oxidation-reduction potential, and temperature to produce a comparison.

9. The method of claim 8, further comprising displaying the comparison of the plurality of water quality parameters to the predetermined set of values.

10. The method of claim 9, wherein the step of displaying the comparison of the plurality of water quality parameters to the predetermined set of values involves a color indication of status for each of the plurality of water quality parameters.

11. The method of claim 6, further comprising determining the oxidation-reduction potential with use of a silver salt gel reference solution within the sensor probe.

12. The method of claim 1, further comprising periodically reconnecting to the wireless internet connection to transmit the plurality of water quality parameters through the wireless internet connection to the cloud storage system.

13. The method of claim 12, wherein the step of periodically reconnecting to the wireless internet connection to transmit the plurality of water quality parameters through the wireless internet connection to the cloud storage system is performed at least once every hour.

14. The method of claim 1, wherein the water quality monitor comprises a power assembly including a battery having a battery life.

15. The method of claim 14, further comprising periodically measuring the battery life during operation of the water quality monitor.

16. The method of claim 15, wherein the step of periodically measuring the battery life during operation of the water quality monitor is performed at least once per hour.

17. The method of claim 1, further comprising filtering debris to allow for unimpeded fluid flow through the water quality monitor.

18. The method of claim 1, further comprising receiving information about a chlorine level of the swimming pool.

19. The method of claim 1, wherein the water quality monitor comprises a base having a first end and a second end, a flow cell jar extending from the second end of the base, and the sensor probe connected to the second end of the base and extending downwardly into the flow cell jar.

20. The method of claim 19, further comprising holding water in the flow cell jar while the water is being tested by the sensor probe.

* * * * *